US008688467B2

(12) United States Patent
Harrison et al.

(10) Patent No.: US 8,688,467 B2
(45) Date of Patent: Apr. 1, 2014

(54) AUTOMATED ANALYSIS OF DATA COLLECTED BY IN-VIVO DEVICES

(75) Inventors: Kyle R. Harrison, Kansas City, MO (US); Lori N. Cross, Kansas City, MO (US); Daniel P. Devers, Kansas City, MO (US); Carlos Hernandez, Kansas City, MO (US); Travis Miner, Kansas City, MO (US); Arthur J. Hauck, Kansas City, MO (US); Timothy Jimenez, Liberty, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 0 days.

(21) Appl. No.: 12/351,612

(22) Filed: Jan. 9, 2009

(65) Prior Publication Data

US 2010/0179820 A1    Jul. 15, 2010

(51) Int. Cl.
*G06Q 50/00*   (2012.01)

(52) U.S. Cl.
USPC .................................................. 705/2; 705/3

(58) Field of Classification Search
None
See application file for complete search history.

(56) References Cited

U.S. PATENT DOCUMENTS

| | | | | |
|---|---|---|---|---|
| 5,941,829 | A * | 8/1999 | Saltzstein et al. ............. | 600/509 |
| 6,442,433 | B1 * | 8/2002 | Linberg ......................... | 607/60 |
| 6,486,588 | B2 | 11/2002 | Doron et al. | |
| 6,878,112 | B2 * | 4/2005 | Linberg et al. ................ | 600/300 |
| 7,257,447 | B2 * | 8/2007 | Cates et al. ..................... | 607/59 |
| 7,261,691 | B1 * | 8/2007 | Asomani ....................... | 600/300 |
| 7,276,905 | B2 | 10/2007 | Tamaroff et al. | |
| 7,389,144 | B1 * | 6/2008 | Osorio et al. .................. | 607/29 |
| 7,792,689 | B2 * | 9/2010 | Duckert .......................... | 705/3 |
| 2005/0283210 | A1 * | 12/2005 | Blischak et al. ............... | 607/60 |
| 2006/0041276 | A1 * | 2/2006 | Chan ................................ | 607/3 |
| 2007/0129774 | A1 * | 6/2007 | Bourget et al. ................ | 607/62 |
| 2007/0168222 | A1 * | 7/2007 | Hoyme et al. .................. | 705/2 |
| 2008/0081958 | A1 * | 4/2008 | Denison et al. ............... | 600/300 |
| 2008/0312961 | A1 * | 12/2008 | Alsafadi ........................... | 705/2 |

(Continued)

OTHER PUBLICATIONS

Separate Computing Device for Medical Device with Computing Capabilities, Sep. 20, 2007, pp. 1-12, http://www.wipo.int/pctdb/en/wo.jsp?WO=2007112384.

(Continued)

*Primary Examiner* — Elaine Gort
*Assistant Examiner* — Jonathan K Ng
(74) *Attorney, Agent, or Firm* — Shook, Hardy & Bacon LLP (57) ABSTRACT

Systems and methods for operably coupling medical device(s) together with an evaluation device such that closed-loop processing may occur are provided. To achieve closed-loop processing, the evaluation device is configured to receive diagnostic information related to physiological attributes of a patient and operational-status information of the medical device(s). Upon receipt of this information, the evaluation device may automatically analyze the data and automatically compose instructions based on the analysis. Analyzing includes comparing the data against content within an electronic medical record (EMR) or applying rules to the data. The rules are built on evidence-based medical procedures consistent with current medical practice. The instructions, when distributed and implemented, invoke actions at the medical device(s), such as dispensing a medication and reprogramming configuration settings, as well as actions at a notification component configured to request a healthcare professional to intervene in a patient's treatment and to provide feedback of medical events.

14 Claims, 6 Drawing Sheets

(56) References Cited

U.S. PATENT DOCUMENTS

| | | | |
|---|---|---|---|
| 2009/0048584 A1* | 2/2009 | Thompson | 604/891.1 |
| 2009/0063193 A1* | 3/2009 | Barton et al. | 705/3 |
| 2009/0171175 A1* | 7/2009 | Li et al. | 600/324 |
| 2009/0234672 A1* | 9/2009 | Dicks et al. | 705/3 |
| 2009/0240526 A1* | 9/2009 | Vesto et al. | 705/3 |
| 2010/0016678 A1* | 1/2010 | Beck et al. | 600/300 |

OTHER PUBLICATIONS

Medical Device, Aug. 15, 2008, pp. 1-6, http://en.wikipedia.org/wiki/Medical_Device.

Electronic Medical Record, Aug. 15, 2008, pp. 1-10, http://en.wikipedia.org/wiki/Electronic_medical_record.

Tim Gee, Microsoft HealthVault: Device Connectivity, Oct. 15, 2007, http://medicalconnectivity.com/2007/10/15/microsoft-health-vault-device-connectivity/.

Peter J. Groen, et al, Implantable Medical Devices and EHR Systems, Jun. 11, 2008, pp. 1-10, http://www.hoise.com/vmw/07/articles/vmw/LV-VM-06-07-5.html.

Technology Overview, Sep. 11, 2008, http://www.s4ms.com/tech_overview.htm.

* cited by examiner

AUTOMATED ANALYSIS OF DATA COLLECTED BY IN-VIVO DEVICES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

Within the medical industry, service providers have employed a variety of tools (e.g., medical devices) to facilitate observation and/or treatment of a patient. Generally, the medical devices are conventional one-operation electronic devices that influence management of one component or system of the patient's body. But, when these electronic devices are operably coupled with the patient and are activated, they function in isolation. That is, the electronic devices are not connected to other devices that can analyze the state of the electronic devices or exert control thereover. For instance, the electronic device may be an in-vivo device implanted into a bladder of a patient. Conventionally, this type of in-vivo device may reset its memory upon passing through airport security equipment. As a result, the patient is required to visit a hospital with the proper equipment to physically connect to the in-vivo device and reconfigure the memory thereof, or the patient is required to communicate with support personnel who manually reset the device to the appropriate settings using a wireless connection technology. When connected to external sources, the electronic devices generally only communicate readings to standalone systems.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Embodiments of the present invention provide systems and methods for uniquely integrating communication technologies (e.g., bidirectional communication), devices, and computer logic to introduce a closed-loop platform that allows one or more medical devices to automatically adjust to environmental factors (e.g., changes in a patient's health, changes in a condition of a medical device, medical-device events, and the like). In addition, the closed-loop platform may link the medical device(s) with an electronic medical record (EMR) associated with the patient and provide communication and interactions not available with traditional EMR-to-device interfaces. Embodiments have several practical applications in the technical arts, including automatically processing data collected by a medical device by comparing the data against relevant content on the EMR. The computing logic may be applied to results of the comparison to ascertain appropriate actions to invoke on the medical devices or elsewhere (e.g., contact the patient, physician, pharmacy, etc.). Accordingly, the closed-loop platform provides a unified architecture where medical devices may work together toward improved patient outcomes, significantly reducing or eliminating human error and variance in medical device care processes. Further, via bidirectional communication, the closed-loop platform may reprogram or update configuration settings of new medical devices incorporated into a patient's healthcare plan, thereby automatically promoting fluid coordination of each device within the closed-loop platform.

More particularly, a first aspect of an embodiment includes one or more computer-readable media accommodated by an evaluation device. Generally, the evaluation device includes computer-useable instructions embodied thereon. Upon execution, the computer-useable instructions perform a method for observing and analyzing physiological attributes of a patient. In instances, the method may involve receiving data from an in-vivo device at the evaluation device. Typically, the data includes diagnostic information that, among other things, characterizes the physiological attributes attained by monitoring the patient utilizing the in-vivo device. Upon receiving the data, a clinical process for analyzing the received data with regard to an EMR may be initiated. In an exemplary embodiment, the clinical process includes, in no particular order, accessing the EMR that is associated with the patient, and comparatively evaluating the data against relevant content of the EMR. In one instance, the relevant content of the EMR includes predefined values that are derived from expected physical attributes of the patient. In this instance, comparatively evaluating the data against relevant content of the EMR may include comparing the diagnostic information against the predefined values, and, based on the comparison, ascertaining whether the diagnostic information fails to satisfy the predefined values. If a failure is detected, a notification of the failure may be provided to one or more interested entities. Based on the comparative evaluation, one or more actions may be induced.

In a second aspect, embodiments are directed toward a computerized method for automatically invoking one or more actions based on an analysis of data communicated from a medical device. Initially, the method involves inspecting data communicated from a monitoring component. As more fully discussed below, the monitoring component may be configured to convey, within the data, diagnostic information of a patient and/or operational-status information that describes events occurring on the medical device (e.g., in-vivo device or ex-vivo device). The method may further include analyzing the data by employing a clinical procedure that includes at least the following steps: implementing rules that are built on evidence-based medical procedures consistent with current medical practice; and applying the rules to the data to identify one or more actions that are responsive to the data. Upon analyzing the data, the method may encompass a procedure of instructing the medical device to implement one or more actions (e.g., reprogramming software, amending treatment, providing alerts, and the like). Typically, the instructions are based on the analysis of the data.

A further aspect of an embodiment takes the form of a computer system capable of enabling analysis of data generated by a monitoring component disposed within a medical device. Initially, the computer system includes a processor coupled to a computer-readable medium that has stored thereon a plurality of computer software components executable by the processor. In embodiments, the computer software components include, at least, a monitoring component, a decision component, and an administering component. The monitoring component may be configured to detect physiological attributes of a patient and events occurring within the medical device for treating the patient. In addition, the monitoring component may be configured to communicate data representing the events and the physiological attributes to a decision component. As more fully discussed below, communication may be bidirectional between components and may make use of any known information-conveyance technologies. The decision component may be configured to ascertain that the data is communicated in a format that is readable thereby. If the data is ascertained to be readable, the decision component may initiate a clinical process that compares the data against an EMR assigned to the patient. And, in embodiments, the decision component may be configured to automatically generate one or more instructions in accordance with an outcome of the comparison. The administering component may be configured to initiate at least one action upon implementing the instructions generated by the decision component.

BRIEF DESCRIPTION OF THE SEVERAL VIEWS OF THE DRAWINGS

Illustrative embodiments of the present invention are described in detail below with reference to the attached drawing figures, which are incorporated by reference herein and wherein.

DETAILED DESCRIPTION

Embodiments provide systems, methods, and computer-readable media for, among other things, operably coupling one or more medical devices (e.g., in-vivo device or ex-vivo device) together with an evaluation device (e.g., a computing device detached from the medical devices or a processing element integral to one or more of the medical devices) such that closed-loop processing may occur. To achieve closed-loop processing, the evaluation device is configured to receive diagnostic information related to physiological attributes of a patient and/or operational-status information of the medical devices. Immediately upon receipt of this information, or at a subsequent time, the evaluation device may automatically analyze the data and automatically compose instructions based on the analysis. These instructions, when distributed and implemented, may cause any number of actions. In one instance, these actions may occur on the medical devices and may include dispensing a medication, reprogramming configuration settings of the medical devices, changing a formatting/security of the information provided by the medical devices, and the like. In other instances, these actions may occur on another device that is not monitoring the patient (e.g., drug-dispensing device) and may include administering treatment to the patient, displaying portions of the information on a graphical user interface (GUI), providing intravenous therapy to the patient, and the like. In yet other instances, these actions may involve automatically generating a notification that is transmitted over any known channel of communication. By way of example only, the notification may request a healthcare professional to intervene in the treatment of the patient, provide information to the patient of a medical event, publish an alert of a critical failure, and the like.

Acronyms and Shorthand Notations

Throughout the description, several acronyms and shorthand notations are used to aid the understanding of certain concepts pertaining to the associated system and services. These acronyms and shorthand notations are solely intended for the purpose of providing a methodology for communicating the various embodiments of the inventions described herein expressed herein and are in no way meant to limit the scope of the present invention. The following is a list of these acronyms:

GUI Graphical User Interface
EHR Electronic Health Record
EMR Electronic Medical Record
LANs Local Area Networks
PDA Personal Digital Assistant
WANs Wide Area Networks Further, various technical terms are used throughout this description. A definition of such terms can be found in *Newtons Telecom Dictionary* by H. Newton, $22^{nd}$ Edition (2006). These definitions are intended to provide a clearer understanding of the ideas disclosed herein but are not intended to limit the scope of the present invention. The definitions and terms should be interpreted broadly and liberally to the extent allowed the meaning of the words offered in the above-cited reference.

As one skilled in the art will appreciate embodiments may be embodied as, among other things, a computer-program product. Accordingly, the embodiments may take the form of a hardware embodiment, a software embodiment, or an embodiment combining software and hardware. In one embodiment, the present invention takes the form of a computer-program product that includes computer-useable instructions embodied on one or more computer-readable media.

Computer-readable media include both volatile and nonvolatile media, removable and nonremovable media, and contemplates media readable by a database, a switch, and various other network devices. By way of example, computer-readable media comprise media implemented in any method or technology for storing information. Examples of stored information include computer-useable instructions, data structures, program modules, and other data representations. Media examples include information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

Methods and systems are provided for utilizing a closed-loop platform to manage a patient's treatment in accordance with a healthcare plan. The healthcare plan serves as a blueprint for guiding the actions that are carried out by the closed-loop platform with regard to changes in the patient's condition or a medical device's operational status. In an exemplary embodiment, the healthcare plan is accessible by the medical devices comprising the closed-loop platform. In this way, the need for a physician to intervene (e.g., to manually input instructions to a medical device) upon each occurrence of a changed condition or operational status is obviated.

As utilized herein, the phrase "healthcare plan" is not meant to be limiting, but may encompass a broad scope of information related to patient history, various treatments, and medicinal practices. Further, the healthcare plan may take any number of forms and may be structured in any manner that allows automatic access thereto. In one instance, the healthcare plan may be generally aggregated into an electronic medical record (EMR), or electronic health record (EHR). As utilized herein, the acronym "EMR" is not meant to be limiting, and may broadly refer to any or all aspects of the patient's medical record rendered in a digital format, and including multiple aspects of data representing the patients interactions with healthcare providers and the healthcare system. Generally, the EMR is supported by systems configured to coordinate the storage and retrieval of individual records with the aid of computing devices. As such, a variety of types of healthcare-related information may be stored and accessed in this way. By way of example, the EMR may store one or more of the following types of information: patient demographics; medical history (e.g., examination and progress reports of health and illnesses); medicine and allergy lists/immunization status; laboratory test results; radiology images (e.g., X-rays, CTs, MRIs, etc.); evidence-based recommendations for specific medical conditions; a record of appointments and physician's notes; and billing records. Accordingly, systems that employ EMR's reduce medical errors, increase physician efficiency, and reduce costs, as well as promote standardization of healthcare.

EMR's may be made up of one or more records that may be centrally located, or distributed across many locations and/or sources. Further, because the EMR's are formatted as electronically, they are usually accessible by computing devices (e.g., medical devices or evaluation devices) over a network. As more fully discussed below, one or more devices of the closed-loop platform may automatically access relevant content within the healthcare-related information encompassed by the EMR. Accordingly, the information of the EMR may be indexed, or configured to be searched for content relevant to a particular request, in order to facilitate satisfying a query.

Upon accessing the EMR, the devices of the closed-loop platform may interrogate the EMR for relevant content or for information that is comparable to the data being collected from events occurring on the patient/medical device. This content and/or information, along with a portion of the collected data, may be input to a clinical process. The clinical process may involve a variety of distinct procedures, as more fully discussed below with reference to FIGS. 2A and 2B. In embodiments, the clinical process, upon execution, returns actions to be completed by components of the closed-loop platform. In an exemplary embodiment, the clinical process implements rules to develop these actions from the collected data in view of the retrieved EMR information. That is, the rules can be used in conjunction with EMR to automatically render accurate responses to collected data that take into account a patient's medical history as well as best medical practices. As utilized herein, the term "rules" is not meant to be limiting, but may encompass any logic or heuristics that can be applied to an input to yield an appropriate output. In one example, the rules may be heuristics that are built on evidence-based medical procedures or plans of care. These procedures are typically consistent with current medical practice, or practices that are approved by a standard's body. In other embodiments, the evidence-based medical procedures may be mined from computerized practice management systems of particular physicians, or groups of physicians. Accordingly, the rules enforce the proper selection of actions to be carried out by the medical device. As discussed below, the rules may be stored on, and employed by, any component(s) (e.g., components 115, 125, and 145 of FIG. 1) that are members of the closed-loop platform.

Figure 1:
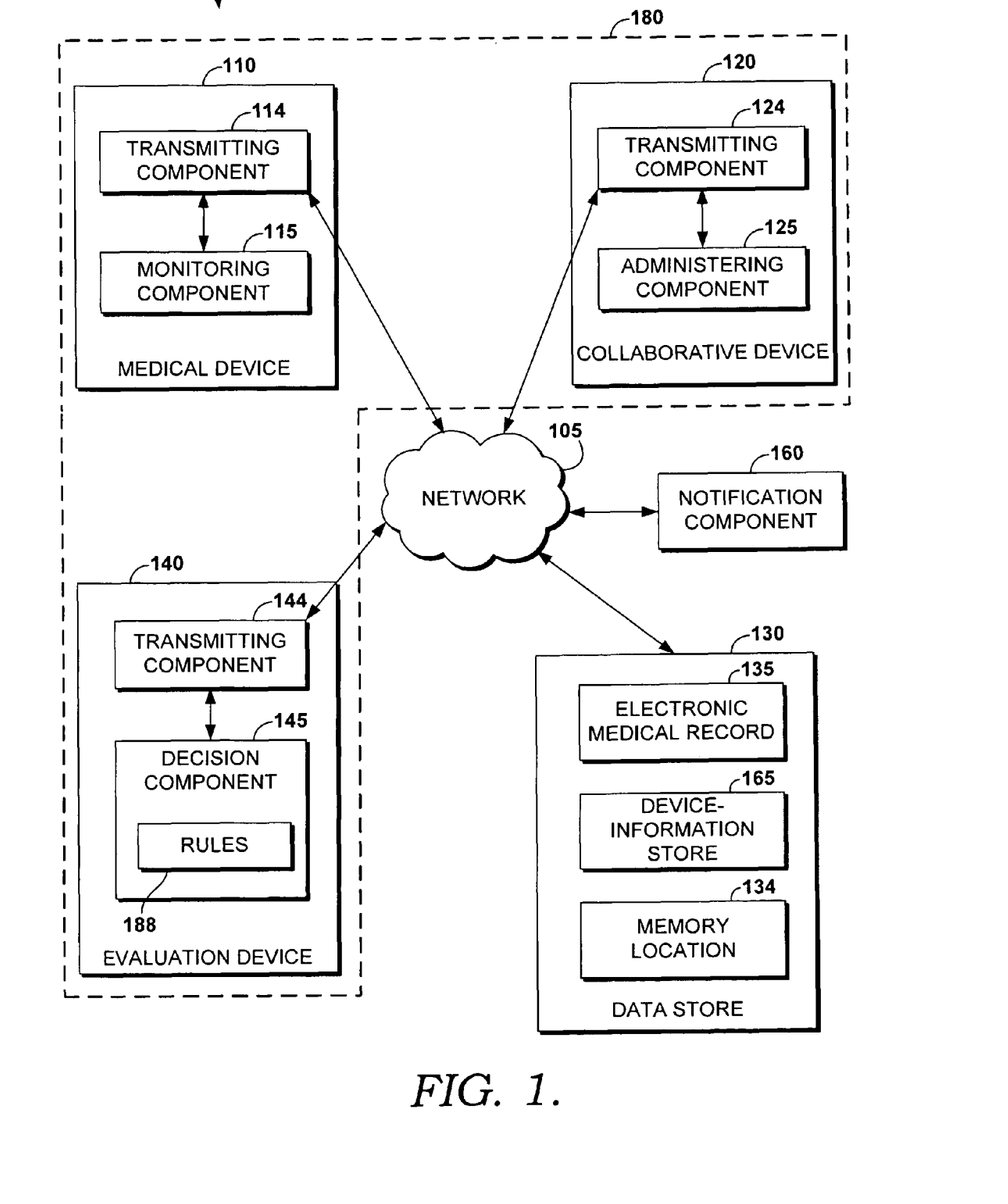
FIG. 1 is a block diagram of an exemplary closed-loop platform with a system architecture suitable for use in implementing embodiments of the present invention.

Referring to the drawings in general, and initially to FIG. 1 in particular, a block diagram of an exemplary closed-loop platform 100 is shown. The exemplary closed-loop platform 100 includes a system architecture suitable for use in implementing embodiments of the present invention. Generally, the closed-loop platform 100 is configured to provide automatic feedback to a medical device 110, a collaborative device 120, and/or a notification component 160 upon collecting and processing data. It should be understood that this and other arrangements described herein are set forth only as examples. Other arrangements and elements (e.g., machines, interfaces, functions, orders, and groupings of functions, etc.) can be used in addition to, or instead of, those shown, and some elements may be omitted altogether. Further, many of the elements described herein are functional entities that may be implemented as discrete or distributed components or in conjunction with other components, and in any suitable combination and location. By way of example, each of the monitoring component 115, the administering component 125, the decision component 145, and the notification component 160 may, at least partially, reside on the medical device 110. Further, various functions described herein as being performed by one or more entities (e.g., devices, components, and the like) may be carried out by hardware, firmware, and/or software. For instance, various functions may be carried out by a processor executing instructions stored in memory, as discussed below.

With continued reference to FIG. 1, the exemplary system architecture of the illustrated instance of the closed-loop platform 100 includes various devices interconnected via a network 105. These devices may include the medical device 110, the collaborative device 120, and an evaluation device 140 operably coupled with each other and to a data store 130. Although, one of each type of device is shown, any number of devices may be employed to achieve the desired functionality within the scope of embodiments of the present invention. Further, although some devices of FIG. 1 are depicted as single blocks, the depictions are exemplary in nature and in number and are not to be construed as limiting (e.g., although only one medical device 110 is shown, many more may be communicatively coupled to the network 105). In addition, one or more of the devices may be combined into a single device that underlies the operation of each of the components installed on the devices (e.g., although the medical device 110 and the collaborative device 120 are shown as individual units, they may be combined to form in-vivo device 385 of FIG. 3).

In embodiments, the medical device 110 represents an object that is useful for diagnostic and therapeutic purposes. Generally, the phrase "medical device" 110 may refer to an instrument, apparatus, appliance, software, material or other article, whether used alone or in combination (e.g., collaborative device 120), that includes software (e.g., monitoring component 115 and transmitting component 114) to carry out its proper purposes on an intended subject. The intended purposes of the medical device 110 include one or more of the following: diagnosis; prevention; monitoring; treatment or alleviation of disease; compensation for an injury or handicap; investigation; or replacement or modification of the anatomy or of a physiological process. Further, the medical device 110 may be applied for the purposes above when the patient is experiencing temporary acute conditions or during long-term chronic conditions. These conditions may be diagnosed and treated by the medical device 110 in both traditional and non-traditional patient settings.

Further, the medical device 110 may be configured as an in-vivo device or an ex-vivo device. In-vivo devices may encompass a wide range of intracorporeal devices, or other devices disposed within the patient. In one exemplary application, in vivo devices are implanted within, or surrounding, tissue of the patient in order to gain knowledge of biological systems and the nature/properties of the tissues. Examples of in-vivo devices may include implantable biosensors, a pacemaker, medication pumps, and ingestible and navigable digital-imaging pills with onboard camera. Ex-vivo devices may encompass a wide range of extracorporeal devices, or other devices that are attached or linked to a patient. In one exemplary application, ex-vivo devices are minimally invasive objects that are proximate to the patient in order to collect data from the patient while inflicting minimal alteration of the natural condition of the patient. By way of example only, ex-vivo devices may be a blood sugar tester for monitoring the patient with diabetes.

In embodiments, the collaborative device 120 may comprise any of the above-discussed embodiments of the medical device 110. In operation, the collaborative device 120 is configured to perform in cooperation with the medical device 110. For instance, the collaborative device 120 may administer medication at a dosage calculated based upon information collected by the medical device 110. In embodiments, the evaluation device 140 may comprise any of the above-discussed embodiments of the medical device 110, or may comprise a computing device. By way of example only and not limitation, the computing device (e.g., computing device 310 of FIG. 3) may be a personal computer, desktop computer, laptop computer, consumer electronic device, handheld device (e.g., personal digital assistant (PDA)), various servers, and the like. It should be noted, however, that embodiments of the present invention are not limited to implementation on such computing devices, but may be implemented on any of a variety of different types of computing devices within the scope of embodiments of the present invention.

Typically, each of the devices 110, 120, and 140 include a computing unit (e.g., central processing unit (CPU), microprocessor, etc.) to support operations of the component(s) running thereon. As utilized herein, the phrase "computing unit" generally refers to a dedicated computing device with processing power and storage memory, which supports operating software that underlies the execution of software, applications, and computer programs thereon. In other embodiments, where the devices 110, 120, and 140 are combined into integrated devices (see FIGS. 5 and 6), a common computing unit is provided that is shared by the components of the integrated devices (e.g., in-vivo device 385 of FIG. 3). In one instance, the computing unit is configured with tangible hardware elements, or machines, that are integral, or operably coupled, to the devices 110, 120, and 140 to enable each device to perform clinical processes and other operations (e.g., therapeutic treatment, diagnostic functions, and the like). In another instance, the computing unit may encompass a processor coupled to the computer-readable medium accommodated by each of the devices 110, 120, and 140. Generally, the computer-readable medium stores, at least temporarily, a plurality of computer software components (e.g., components 115, 125, 145, and 160) that are executable by the processor. As utilized herein, the term "processor" is not meant to be limiting and may encompass any elements of the computing unit that act in a computational capacity. In such capacity, the processor may be configured as a tangible article that processes instructions. In an exemplary embodiment, processing may involve fetching, decoding/interpreting, executing, and writing back instructions (e.g., saving the results of the execute step to the computer-readable memory).

Also, beyond processing instructions, the processor may transfer information to and from other resources (not shown) that are integral to, or disposed on, the devices 110, 120, and 140. Generally, resources refer to software and hardware mechanisms that enable a device to perform a particular function. By way of example only, the resources may include biosensors that can test indicators or symptoms of disease and report the results of the tests to the monitoring component 115 as diagnostic information. In another example, the resources may include an internal mechanism for regulating a release of a drug (e.g., dispensing insulin to a diabetes patient at a predetermined dosage) based on the diagnostic information received by the administering component 125. In yet other examples, the resources may comprises one or more of the following mechanisms: imaging apparatuses; databases; printing devices; paging systems; audio alert devices; and media-display units.

As indicated by reference numeral 180, the devices 110, 120, and 140 may be joined together to form a team of devices within the closed-loop platform 100. The team 180 may include any of the devices 110, 120, and 140, or any other devices that interact with the illustrated devices via the network 105. The team 180 of devices may be constructed upon initiation of a particular treatment of a patient. Constructing the team 180 allows members thereof to fluidly communication with each other and coordinate activities with little oversight. Upon constructing the team 180, the member devices are allowed to automatically communicate with other devices in order to work together and to make real-time adjustments as directed by EMR 135. Further, team 180 of devices may be reconfigured (e.g., the decision component 145 is updated with the latest interoperability standards) to allow other new devices with more recent technology to join and collaborate with the current member devices.

The data store 130 is generally configured to store at a memory location 134 data generated and conveyed from at least one of the devices 110, 120, and 140 discussed below. In various embodiments, such data may include, without limitation, diagnostic information (e.g., a characterization of physiological attributes attained by monitoring the patient), and operational-status information that describes events occurring on a device (e.g. whether the medical device 110 has entered a failure mode). Further, the data store 130 may be configured to store data related to one or more of the devices 110, 120, and 140 at a device-information store 165. The data stored at the device-information store 165 may include such information as predefined properties of a device, operating ranges in which a device functions, configuration settings of the device, and the like. As more fully discussed below, the decision component 145 may compare operational-status information against other data stored at the device-information store 165 in order to determine whether the medical device 110 has entered a failure mode.

In addition, the data store 130 may be configured to be searchable for, or provide suitable access to, the data stored thereon. For instance, the data store 130 may be searchable for relevant content within an EMR 135 associated with a patient being treated by the closed-loop platform 100. It will be understood and appreciated by those of ordinary skill in the art that the information stored in the data store 130 may be configurable and may include any information relevant to the processes executed to achieve proper execution of the closed-loop platform 100 (e.g. clinical process 240 of FIG. 2A). The content and volume of such information are not intended to limit the scope of embodiments of the present invention in any way. Further, though illustrated as a single, independent component, the data store 130 may, in fact, be a plurality of databases, for instance, a database cluster, portions of which may reside on one or more of the devices 110, 120, and 140, another external computing device (not shown), and/or any combination thereof. Further, the data store 130 may be a plurality of databases that each accommodates the electronic medical record 135, the device-information store 165, and the memory location 134 individually.

As discussed above, computing unit(s) of the devices underlie the operation of the computer software components. Exemplary components may include the monitoring component 115, the administering component 125, and the decision component 145 that include, or has access to, rules 188. Initially, in embodiments, the monitoring component 115 acts in a passive capacity to acquire information and convey that information as data via a transmitting component 114. In other embodiments, the monitoring component 115 is configured to actively interrogate predetermined resources of information, such as biosensors, to gather the data. In one instance, the monitoring component 115 is tuned to track particular information related to the health of the patient (e.g., physiological test results, digital images, sound data). In another instance, the monitoring component 115 is tuned to track the operational status of the medical device 110 (e.g., a fault self-reported by the medical device 110). Tuning the monitoring component 115 may include programming the configuration settings of the monitoring component 115. These configuration settings may be reprogrammed based on the results of the clinical process, as more fully discussed below with reference to the FIG. 2B.

In an exemplary embodiment, the monitoring component 115 may be configured to detect physiological attributes of a patient and events occurring within the medical device 110. The monitoring component 115 may be further configured to communicate data representing the events and the physiological attributes to the decision component 145. Communicating may include distributing the data to the network 105 via a transmitting component 114 located on the medical device 110. In an exemplary embodiment, the transmitting component 114 is further configured to append an identifier of the patient and specifications of the medical device 110 to the data. In operation, this identifier allows the decision component 145 to access an appropriate data store 130 when carrying out the clinical process. For instance, the decision component 145 may discover the EMR 135 assigned to the patient based on the patient identifier and may access an appropriate device-information store 165 based on the medical device specifications.

Further, in embodiments, the decision component 145 is configured to ascertain that the data is communicated in a format that is readable. If the data is readable, the decision component 145 may either store the data or process the data. In an exemplary embodiment, processing the data includes initiating a clinical process. The clinical process, as described herein, is not meant to be limited to a particular set of procedures, but encompasses any procedures that would occur to achieve certain results. These results may include providing an analysis of the data with respect to the EMR 135, evaluating a status of the patient/medical device 110, and developing instructions that induce the devices 110, 120, and 140 to take particular actions. In one instance, providing an analysis of the data with respect to the EMR 135 involves comparing the data against an electronic medical record (EMR) associated with the patient. Providing an analysis may also involve medically generating one or more instructions in accordance with an outcome of the comparison. Procedures encompassed by the clinical process, and the results achieved by these procedures, are discussed more fully below with respect to FIGS. 2A and 2B.

The decision component 145, in embodiments, can access rules 188 for guiding the execution of the clinical process and determining a proper course of action upon analyzing the data transmitted from the monitoring device 115. In an exemplary embodiment, the rules 144 represent heuristics or logical steps that are built on evidence-based medical procedures consistent with proper medicinal practice, as more fully discussed above. In one instance of executing the clinical process, the rules 144 may retrieve an expected operating range based on an identity of the medical device 110, and compare the data received from the medical device 110 against the expected operating range, thereby filtering transient information. In another instance of executing the clinical process, the rules 144 may retrieve patient information from the EMR 135 based on an identity of the patient, and compare data (e.g., diagnostic information) received from the medical device 110 against patient information, thereby ensuring subsequent medical actions are tailored to the patient's physiological characteristics.

The administering component 125 is generally configured to initiate at least one action upon implementing one or more instructions. These instructions may be provided by the monitoring component 115 on the medical device 110, by the decision component 145 on the evaluation device 140, or by any other components (e.g. the electronic medical record number 135) within the closed-loop platform 100 that are operably coupled with the administering component 125. The action(s) initiated by the administering component 125 include a broad range of actions that may be carried out by the collaborative device 120, the medical device 110, and/or the data store 130. As such, the administering component 125 may reside on any of the devices 110, 120, 130, and 140 within the closed-loop platform 100. In one instance, the action(s) may include storing, at least temporarily, portions of the data in the memory location 134. In another instance, the action(s) may include directing the monitoring component 115 to continue to observe the patient and provide diagnostic information as well as self-report medical-device events affecting the medical device 110. In yet another instance, the action(s) may include causing the medical device 110 or the collaborative device 120 to dispense treatment to the patient, as more fully discussed below with reference to FIG. 3.

The notification component 160 is generally configured to implement one or more instructions issued by the components 115, 125, and/or 145. Implementing the instructions may encompass a large scope of actions, such as automatically publishing a communication that solicits assistance from a healthcare entity (e.g., patient, physician, EMR 135, etc.). In this embodiment, the notification component 160 is operably coupled to, or integrated with, a device for carrying out the step of publishing. When publishing involves displaying the communication, the device may be a monitor. When publishing involves alerting a physician, the device may be a pager system, an e-mail system, a telephone network, and the like, that can transmit the communication to the appropriate physician. When publishing involves notifying the patient, the device may include a computer that can retrieve contact information (e.g. phone number, address, etc.) of the patient and facilitate transmitting the communication by addressing a message utilizing the contact information (e.g. calling the identified phone number).

Although three different configurations of the notification component 160 have been described, it should be understood and appreciated by those of ordinary skill in the art that other types of suitable configurations and devices that provide a notification that prompts human intervention may be used, and that embodiments of the present invention are not limited to those embodiments of the notification component 160 described herein. For instance, the notification component 160 may be configured to recognize that the communication to be conveyed relates to an urgent medical situation, and accordingly, to automatically select a proper form of communication to rapidly engage an appropriate healthcare entity. In other embodiments, publishing the communication may encompass one or more of the following actions: displaying a graphical user interface at a computing device (see GUI 320 on computing device 310 of FIG. 3), conveying an e-mail, initiating an automated phone call, sending a page, providing feedback to a patient, ordering a drug at a pharmacy (see reference numeral 425 of FIG. 4), or alerting an insurance company (see reference numeral 445 of FIG. 4) of the treatment required by the instructions.

In an exemplary embodiment of the closed-loop platform 100, the monitoring component 115, the decision component 145, and the administration component 125 are each operably coupled to transmitting components 114, 124, and 144 that facilitate bidirectional communication therebetween. This bidirectional communication promotes real-time electronic interaction between the components 115, 125, and 145 via the network 105. The transmitting components 114, 124, and 144 may comprise any software or hardware that is capable of facilitating communication between devices. By way of example only, the transmitting components 114, 124, and 144 may include transceiver elements that are tailored to allow for communication across a wireless network. In addition, the transmitting components 114, 124, and 144 may promote interoperability between the various devices. Generally, interoperability refers to the ability of different information technology systems and software applications to communicate, to exchange data accurately, effectively, and consistently, and to use the information that has been exchanged. For instance, the transmitting components 114, 124, and 144 may reformat data such that, upon conveyance, the data may be understood between practicing physicians, pharmacies, insurance companies, and hospitals without need for further semantic interpretation or translation. By way of example, reformatting the data may include converting the data to machine-interpretable data (e.g., structured messages, standardized content, and the like) for automated transfer between initially incompatible devices.

In this way, the transmitting components 114, 124, and 144 act as communications interfaces between the components 115, 125, and 145 and the network 105. Further, the transmitting components 114, 124, and 144 allow for convergence of the medical device 110 (e.g., in-vivo devices), the EMR 135, the evaluation device 140, and the collaborative device 120 (e.g., ex-vivo devices) with emerging wireless technologies such as broad spectrum Internet and Bluetooth™. Advantageously, the devices 110, 120, and 140, as well as the EMR 135, can automatically work in concert with each other and other medical devices, thus, significantly reducing or eliminating human error and variance in acute and chronic care management processes. In addition, the ability to wirelessly couple the devices 110, 120, and 140 to the EMR 135 provides greater mobility for patients, thereby improving care management for chronic conditions of patients in nontraditional patient care settings, such as the home or office.

Beyond formatting the communications distributed from each of the devices 110, 120, and 140, the transmitting components 114, 124, and 144 may transmit the communications according to a communication scheme. The communication scheme may direct the transmitting components 114, 124, and 144 to send the communications in real-time, at predefined time frames, at regular intervals, upon the issuance of a request for the data, upon the detection of a particular piece of data that triggers a communication, upon aggregating and storing the data within a device (if provided with a data store), etc. The communication scheme may also instruct the transmitting components 114, 124, and 144 on how to send the data. These instructions may be based on a predefined hierarchy of communication pathways that are employed by devices 110, 120, and 140. Communication pathway(s) may be selected from the predefined hierarchy upon detecting changes in a medical device's operating environment. For instance, the communication scheme may articulate that a primary pathway of communication from one or more of the transmitting components 114, 124, and 144 is over a wireless connection supported by the network 105. Upon detecting changes in the medical device's 110 operating environment (e.g., a disruption in a network 105 carrying the wireless communication, or a disconnection of the other devices 120 and 140), the communication scheme may instruct one or more of the transmitting components 114, 124, and 144 to exercise an auxiliary pathway (e.g., wired connection over landlines) within the network 105. Accordingly, the communication scheme promotes substantially continuous communication of the data and provides an additional layer of safety for the patient.

Further, the transmitting components 114, 124, and 144 of the exemplary system architecture of the closed-loop platform 100 may be interconnected by any method known in the relevant field. For instance, the medical device 110 and the collaborative device 120 may be operably coupled via a distributed communications environment supported by the network 105. In embodiments, the network 105 may include, without limitation, one or more local area networks (LANs) and/or wide area networks (WANs). Such networking environments may be commonplace in offices, enterprise-wide computer networks, intranets, and the Internet. In addition, many more components/devices/entities beyond those shown in FIG. 1 (e.g., mobile device 315 of FIG. 3) may be operably coupled to network 105.

In yet other embodiments, the network 105 may couple components 115, 125, 134, 135, 145, and 165, thereby forming a distributed computing environment where tasks are performed by remote-processing devices (e.g., evaluation device 140) that are linked through appropriate connections. These connections may be established by wired technologies, wireless technologies, or a combination thereof. Examples of particular wired embodiments, within the scope of the present invention, include USB connections and cable connections. Examples of particular wireless embodiments, within the scope of the present invention, include a near-range wireless network and radio-frequency technology. It should be understood and appreciated that the designation of "near-range wireless network" is not meant to be limiting, and should be interpreted broadly to include at least the following technologies: negotiated wireless peripheral (NWP) devices; short-range wireless air interference networks (e.g., wireless personal area network (wPAN), wireless local area network (wLAN), wireless wide area network (wWAN), Bluetooth™, and the like); wireless peer-to-peer communication (e.g., Ultra Wideband); and any protocol that supports wireless communication of data between devices. Additionally, persons familiar with the field of the invention will realize that a near-range wireless network may be practiced by various data-transfer methods (e.g., satellite transmission, telecommunications network, etc.) that are different from the specific illustrated embodiments. Therefore it is emphasized that embodiments of the connections between components are not limited by the examples described, but embrace a wide variety of methods of communications.

Figure 2A:
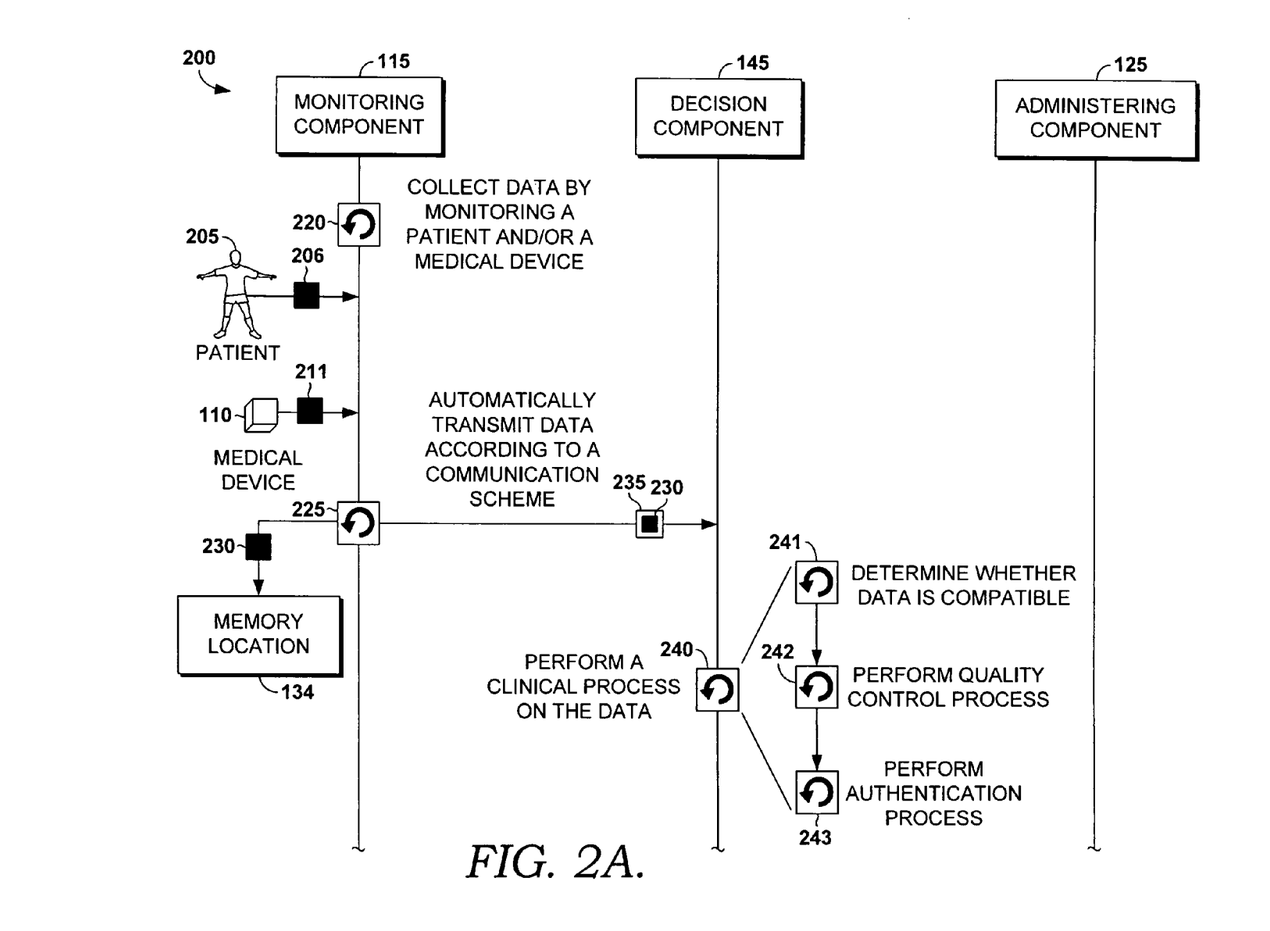
FIGS. 2A and 2B are operational flow diagrams illustrating a high-level overview of an exemplary technique for managing a closed-loop platform in a wireless network environment, in accordance with an embodiment of the present invention.
Figure 2B:
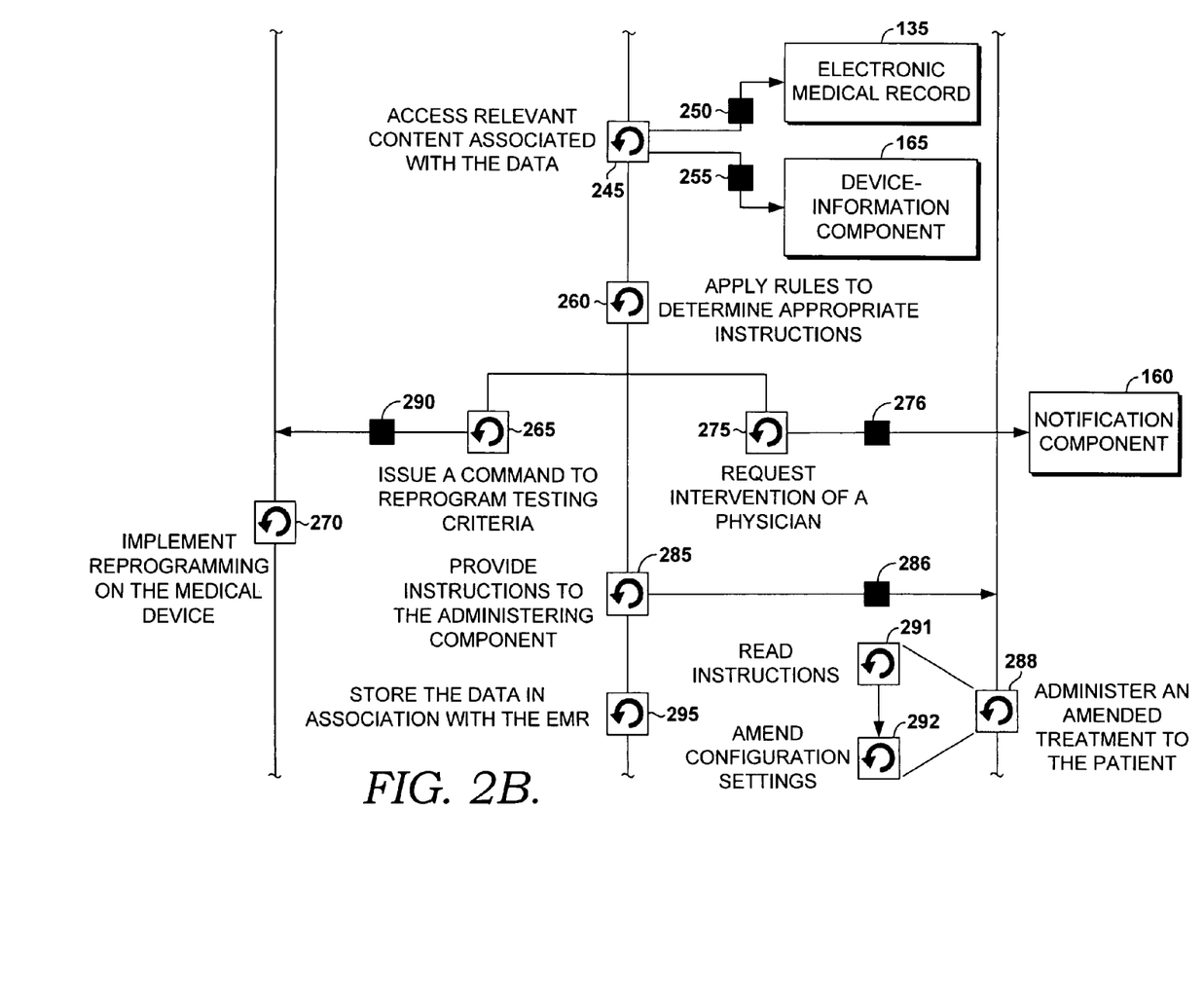

Embodiments of the interaction between the devices 110, 120, and 140 linked together as the team 180 operating within the closed-loop platform 100 will now be described with reference to FIGS. 2A and 2B. FIGS. 2A and 2B show operational flow diagrams 200 illustrating a high-level overview of an exemplary technique for managing the closed-loop platform in a wireless network environment, in accordance with an embodiment of the present invention. In describing various embodiments of the present invention, similar components and devices are labeled with consistent reference numerals. For example, the monitoring component 115 of FIG. 1 is consistently labeled as such in FIGS. 2A and 2B. But, persons familiar with the field of the invention will realize that the process of observing and treating a patient may be practiced by various components which are different from the specific illustrated components. Therefore it is emphasized that the present invention is not limited only to embodiments having the consistent components but embraces a wide variety of components which fall within the spirit of the following claims.

Initially, the monitoring component 115 is configured to collect data 230 by monitoring a patient 205 and/or the medical device 110 (e.g., the medical device 110 of FIG. 1), as depicted by process 220. The process 220 may involve collecting diagnostic information 206 from the patient 205, and may involve collecting operational-status information 211 from the medical device 110. The monitoring component 115 may also execute a process 225 that automatically transmits data 230 according to a communication scheme. The communication scheme, as more fully discussed above, may govern where the data 230 are transmitted from the monitoring component 115. In one instance, the data 230 may be transmitted for storage at the memory location 134. In another instance, the data 230 may be transmitted to the decision component 145 for analysis thereby. In yet another instance, the data 230 may be transmitted directly to the administering component 125 to invoke an action that influences the care of the patient 205.

The process 225 may include appending the data 230 with an indicia 235. The indicia 235, in one embodiment, may include an identity of the patient 205. In this embodiment, the identity of the patient 205 may be used to map the data 230 to, or discover, an appropriate EMR 135 assigned to the patient 205. In another embodiment, the indicia 235 may include an identity or a type of the medical device 110 that is observing the patient 205. In this embodiment, the identity or type of the medical device 110 may be used to target information related to the particular medical device 110 (e.g., at the device-information store 165 of FIG. 1). As such, appropriate reference ranges and/or medical device specifications that are specific to the medical device 110 may be accessed to accurately interpret the data 230 being received from the monitoring component 115.

Upon receiving the data 230 at the decision component 145, the clinical process 240 may be performed on the data 230. As illustrated, the clinical process 240 may be performed at the decision component 145; however, the clinical process 240 may be fully or partially performed on any of the components mentioned herein. In embodiments, the clinical process 240 may include one or more of the following procedures: determining whether the data 230 is compatible with the decision component 145, as depicted by procedure 241; performing a quality control process, as depicted by procedure 242; and performing an authentication process, as depicted by procedure 243. During execution of the procedure 241, the decision component 145 may perform at least one of the steps of ascertaining a format of the data 230, determining whether the format is comparable with the expected format, and, at least temporarily, storing the data 230. When it is determined that the format is incompatible, upon comparison with the expected format, the decision component 145 may attempt to adjust the incompatible format of the data 230, or other outputs of the monitoring component 115, being communicated from the monitoring component 115 in order to align with the expected format. In addition, the decision component 145 may temporarily store the incompatibly formatted data 230 in a temporary memory location within the closed-loop platform for future access. When it is determined that the format is compatible, upon comparison with the expected format, the decision component 145 may analyze the data 230 and generate instructions based thereon.

The quality control process 242 is utilized to validate the data 230 being communicated from monitoring component 115. In embodiments, the quality control process 242 involves confirming that the data 230 is genuine by collecting information related to the medical device 110 transmitting the data 230. By way of example, collecting information may include reading configuration settings from the medical device 110 (e.g., provided in the operational-status information 211) and confirming that the data 230 is accurate based on those configuration settings. The authentication process 243 may be utilized to verify that the medical device 110 is actually the source of the data 230 and to interpret the data 230. Interpreting the data 230 may involve decoding a security measure imposed by the medical device 110 on the data 230 that protects against impermissible access thereto.

With reference to FIG. 2B, the decision component 125 may continue carrying out the clinical process 240 by accessing relevant content associated with the data 230, as depicted by procedure 245. In one instance, accessing relevant content involves interrogating the EMR 135 to gather content 250 therein that is pertinent to the patient 205 or relevant to the physiological characteristics of the patient 205. In another instance, accessing relevant content involves extracting device specifications 255 from the device-information component 165.

As depicted at process 260, rules (e.g., the rules 188 of FIG. 1) are applied to the data 230, to the relevant content, or to other information associated with the data 230. Upon applying the rules, instructions may be developed based on the data 230. In one embodiment, developing instructions may include comparatively evaluating the data 230 against the content 250 of the EMR 135. In one instance, comparatively evaluating includes comparing the diagnostic information 206 of the patient 205 against predefined values within the EMR 135. If it is determined, upon comparison, that the diagnostic information 206 does not satisfy the predefined values, intervention of the physician may be requested, as depicted by procedure 275. In this instance, the request 276 may be transmitted to the notification component 160 where it is published to an appropriate healthcare entity.

In another embodiment, developing instructions may include comparatively evaluating the data 230 against predefined values associated with functional aspects of the medical device 110. In one instance, the operational-status information 211 of the medical device 110 may be compared against device specifications 255 stored at the device-information component 165. If it is determined, upon comparison, that the operational-status information 211 does not satisfy the device specifications 255, a command may be issued to modify configuration settings of the medical device 110 and/or monitoring component 115. By way of example, the command 290 may be issued to reprogram testing criteria utilized by the monitoring component 115, as depicted at process 265. Upon receiving the command 290 to reprogram, monitoring component 115 may implement a process 270 to reprogram the configuration settings of the medical device 110. By way of example, reprogramming the medical device 110 may involve adjusting the testing criteria such that the sampling frequency of the physiological attributes of the patient 205 is altered. In another example, reprogramming the medical device 110 may involve adjusting the testing criteria such that the determination of which physical attributes of the patient 205 selected for observation is revisited.

In yet another embodiment, developing instructions may include providing the instructions 286 to the administering component 135, as depicted by process 285. Upon receiving the instructions at the administering component 125, a process 288 may be carried out that invokes action(s) at the medical device 110 and/or at the collaborative device 120. These actions may include administering an amended treatment to the patient 205, or any other actions that affect treatment of the patient 205 described herein. In a particular embodiment, the process 288 may be carried out by a procedure 291 that involves reading the instructions 286 and a procedure 292 that involves amending configuration settings of the medical device 110 and/or the collaborative device 120. Further the data 230 is to be stored in association with the EMR 135, as depicted by process 295.

This exemplary system architecture of the closed-loop platform 100 of FIG. 1 is but one example of a suitable environment that may be implemented to carry out aspects of the present invention, and is not intended to suggest any limitation as to the scope of use or functionality of the invention. Neither should the illustrated exemplary system architecture of FIGS. 1, 2A, and 2B be interpreted as having any dependency or requirement relating to any one or combination of the components 114, 115, 124, 125, 134, 135, 144, 145, 160, and 165 as illustrated. In some embodiments, one or more of the components 114, 115, 124, 125, 134, 135, 144, 145, 160, and 165 may be implemented as stand-alone devices. In other embodiments, one or more of the components (e.g., the monitoring component 115, the decision component 145, and the administering component 125) may be integrated directly into the one or more of the devices 110, 120, and 140. It will be understood by those of ordinary skill in the art that the components 114, 115, 124, 125, 134, 135, 144, 145, 160, and 165 illustrated in FIGS. 1, 2A, and 2B are exemplary in nature and in number and should not be construed as limiting.

Accordingly, any number of components may be employed to achieve the desired functionality within the scope of embodiments of the present invention. Although the various components of FIGS. 1, 2A, and 2B are shown with lines for the sake of clarity, in reality, delineating various components is not so clear, and metaphorically, the lines would more accurately be grey or fuzzy. Further, although some components of FIGS. 1, 2A, and 2B are depicted as single blocks, the depictions are exemplary in nature and in number and are not to be construed as limiting (e.g., although only one medical device 110 is shown, many more may be communicatively coupled to the evaluation device 140)

Figure 3:
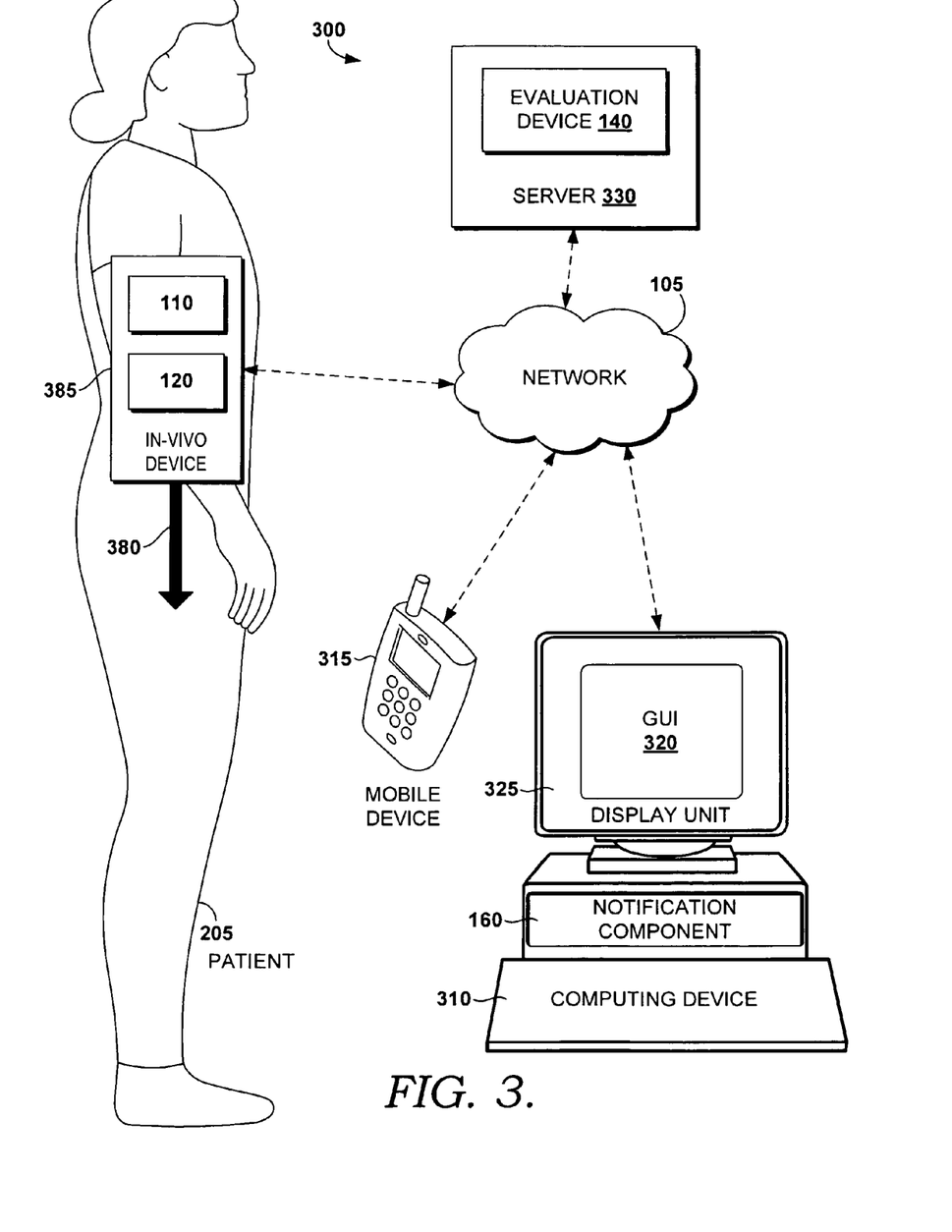
FIGS. 3 and 4 are graphical depictions illustrating applications of exemplary closed-loop platforms to healthcare settings, in accordance with embodiments of the present invention.
Figure 4:
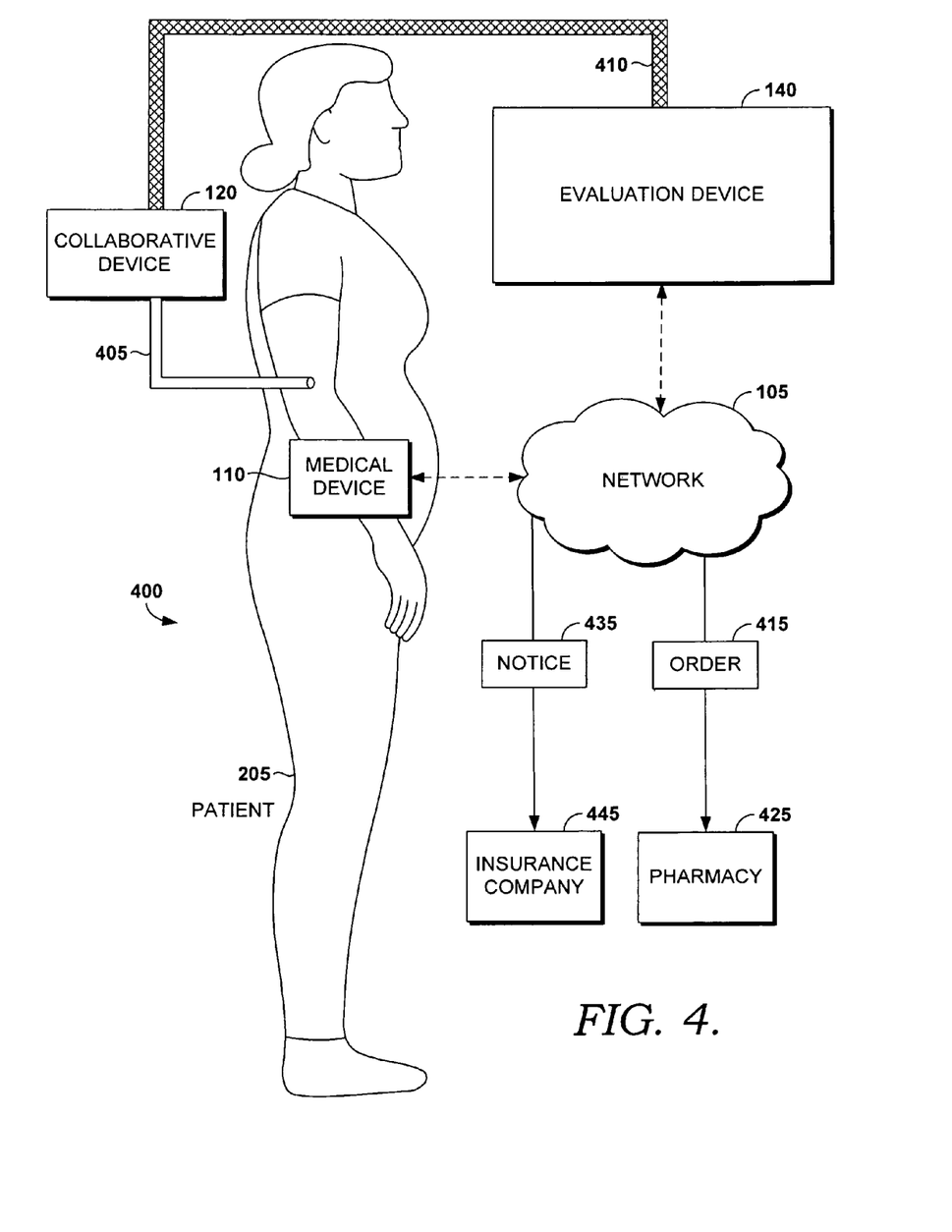

Turning now to FIGS. 3 and 4, particular examples of specific teams of devices and specific modes of operation of the devices are illustrated and described for explanation purposes only. These particular examples are not to be construed as limiting. Initially, FIG. 3 shows a graphical depiction of an exemplary closed-loop platform 300 applied to a healthcare setting, in accordance with embodiments of the present invention. Generally, this illustrative closed-loop platform 300 is configured to treat a patient 205 afflicted with the chronic pain condition utilizing an in-vivo device 385. By way of example, the in-vivo device 385 may be an implantable medication-dispensing pump that continuously dispenses a prescribed drug at a particular dosage. In addition, the in-vivo device 385 is completely contained within the patient 205, and conventionally, would offer no (or limited) electronic communication, or physical indication (e.g., visual/auditory alert) of a failure or of a depletion in the drug it dispenses. However, the in-vivo device 385 contemplated by this embodiment of the present invention includes assorted components of the medical device 110 and the collaborative device 120 as described above with respect to FIG. 1. These components may comprise a monitoring component, an administering component, and transmitting component and may function in conjunction with each other.

If in-vivo device 385 depletes itself of the prescribed drug, the patient 205 will be rendered incapacitated. Accordingly, the monitoring component is configured to watch medical-device events occurring on the in-vivo device 385 and collect operational-status information based on the events. The transmitting component may wirelessly convey the operational-status information as data through the network 105 to the evaluation device 140 residing on a remote server 330. Upon detecting that the in-vivo device 385 is running low on, or depleted of, the drug, the evaluation device 140 may provide a communication through the network 105 to a mobile device 315, a computing device 310, or any other device known by those of ordinary skill in the art that may be connected to a network.

Generally, the mobile device 315 may be any type of device having communications capability. For instance, the mobile device 315 may be, or variously referred to as, a handheld device, mobile handset, consumer electronics device, pager, cell phone, personal digital assistant (PDA) unit, and the like. In addition, each mobile device 315 is provisioned with hardware that facilitates transmission and receptions of signals wirelessly over the network 105. These signals may include the communication from the evaluation device 140 located at the remote server 330, or communications sent directly from the transmitting component residing on the in-vivo device 385. In one embodiment, the mobile device 315 is capable of alerting the user that the communication has arrived and/or presenting content of communication to the user. As such the user (e.g., a physician treating the patient 205, or a pharmacy employee) is notified that the drug is to be refilled within the in-vivo device 385.

The communication across the network 105 may also be received at the notification component 160 accommodated by the computing device 310. In one instance, the notification component 160 may reveal content of the communication as a graphical user interface (GUI) 320 rendered on a display unit 325. Accordingly, the state of the in-vivo device 385 (e.g., empty medication-dispensing pump) may trigger an appropriate entity to initiate a procedure to refill the in-vivo device 385, thereby avoiding a series of events that would lead to discomfort and/or to hospitalization of the patient 205. In this way, the monitoring component, the evaluation device 140, and the notification component 160 are allowed to interact, make determinations based on the interaction, and implement the determinations automatically even though these components each reside on a separate device. The notification of a healthcare entity may be practiced by various devices which are different from the specific illustrated embodiment and may employ various media for providing the notification. Therefore it is emphasized that the embodiments of the present invention are not limited to the depiction of the notification component 160 on a computing device 310, but embrace a wide variety of mechanisms for requesting intervention of a healthcare entity.

In another scenario, the in-vivo device 385 is adapted to dispense a hard-to-regulate drug, such as blood thinners. Generally, hard-to-regulate drugs are released to the patient 205 based on a current condition of the patient 205. If the current condition of the patient 205 is unknown, there is a high potential that over-treating or under-treating may occur. Each of these instances may result in harm to the patient 205. Conventionally, frequent manual testing was conducted on the patient 205 to reduce errors in treatment. Based on the manual testing, the dosage of medication dispensed by an isolated in-vivo device was manually adjusted.

But, in an exemplary embodiment of the present invention, the monitoring device may automatically collect diagnostic information, such as a measurement of blood coagulation capabilities, and convey that information as data to the evaluation device 140 via the network 105. The evaluation device 140 may access the EMR assigned to the patient 205 and compare the diagnostic information against relevant content of the EMR. The relevant content may comprise blood coagulation levels determined by a physician to be appropriate. If the measured blood coagulation level of the patient 205 falls outside these levels, then instructions are developed by the evaluation device 140 and transmitted to the administering component integrated within the in-vivo device 385, which carries out the instructions. By way of example, if the coagulation level of the blood is measured as being above the preestablished levels, then the evaluation device 140 may instruct the administering component to invoke a particular action. This particular action may include internally injecting 380 blood thinner into the patient 205. In other embodiments, the particular action may include reprogramming the configuration settings of the in-vivo device 385 to automatically inject 380 the blood thinner at more frequent increments of time. In this way, the close-loop platform 300 takes an active response to data provided by the monitoring device without the intervention of the physician.

Turning now to FIG. 4 an illustrative closed-loop platform 400 is shown that is configured to treat a patient 205. The closed-loop platform 400 includes an in-vivo medical device 110, an evaluation device 140, and an ex-vivo collaborative device 120. By way of example, the medical device 110 may be a fetal monitor completely contained within the patient 205, and the collaborative device 120 may be a medication-dispensing device (e.g., facilitating intravenous therapy). As illustrated in FIG. 4, because the medical device 110 is completely contained within the patient 205, it is configured to communicate wirelessly over the network 105. In contrast, because the collaborative device 120 and evaluation device 140 are both external to the patient 205 and within the same patient care setting, these devices may be operably coupled with a wired connection 410. Further, the collaborative device 120 may include a channel 405 for transporting medication to the patient 205.

In operation, the medical device 110 may passively detect physiological characteristics of the patient 205 (e.g., a pregnant woman) and of her prenatal baby. If the medical device 110 detects an irregularity with the prenatal baby or its mother, an indication of the irregularity may be communicated to the evaluation device 140 for analysis through the clinical process. The evaluation device 140 may then develop instructions based on an outcome of the clinical process, where the instructions invoke an action at the collaborative device 120, an insurance company 445, and/or a pharmacy 425. Upon receiving the instructions at the collaborative device 120 via the wired connection 410, the collaborative device 120 may actively implement the instructions by increasing, decreasing, or maintaining an amount of medication being dispensed to the patient 205 via the channel 405. In one embodiment, implementing the instructions entails reprogramming software or adjusting configuration settings on the collaborative device 120. Reprogramming the software (e.g., adjusting protocols, writing a portion of the logic, etc.) ensures the collaborative device 120 properly and automatically carries out the instructions of the evaluation device 140 independently. That is, upon reprogramming the software of the collaborative device 120, the collaborative device 120 will consistently dispense medication at the increased or decreased rate, in accordance with the instructions, without additional direct commands from the evaluation device 140 and without intervention of a physician.

Invoking an action at the insurance company 445 may include providing instructions from the evaluation device 140 in the form of a notice 435. As discussed above, the instructions may be based on the data transmitted wirelessly from the medical device 110, or may be based on any other information or logic (e.g., EMR, rules, etc.). The notice 435 may alert the insurance company 445 that a new medication, or more medication, is necessary for proper treatment of the patient 205. In response, the insurance company 445 may recommend a comparable generic drug or submit funds to pay for the medication.

Invoking an action at the pharmacy 425 may include providing instructions from the evaluation device 140 in the form of an order 415. As discussed above, the instructions may be based on the data transmitted wirelessly from the medical device 110, or may be based on operational-status information (e.g., current levels of medication) of the collaborative device 120 that is transported as data therefrom. The order 415 may notify the pharmacy 425 to order more of a particular medication to refill the collaborative device, or may adjust a timing of a standing order for medication to correspond with the new medication-dispensing rate of the collaborative device 120.

Although various different scenarios for automatically carrying out instructions, both passively and actively, have been described, it should be understood and appreciated by those of ordinary skill in the art that other types of suitable scenarios may be available using the closed-loop platform technology, and that embodiments of the present invention are not limited to those scenarios described herein. For instance, based on a severity of the patient's condition and/or the state of the medical device, the instructions may automatically request an ambulance (by accessing the patient's contact information), schedule a doctor's appointment (by accessing the patient's electronic calendar), and the like, while the patient is working in his/her office or at home.

Figure 5:
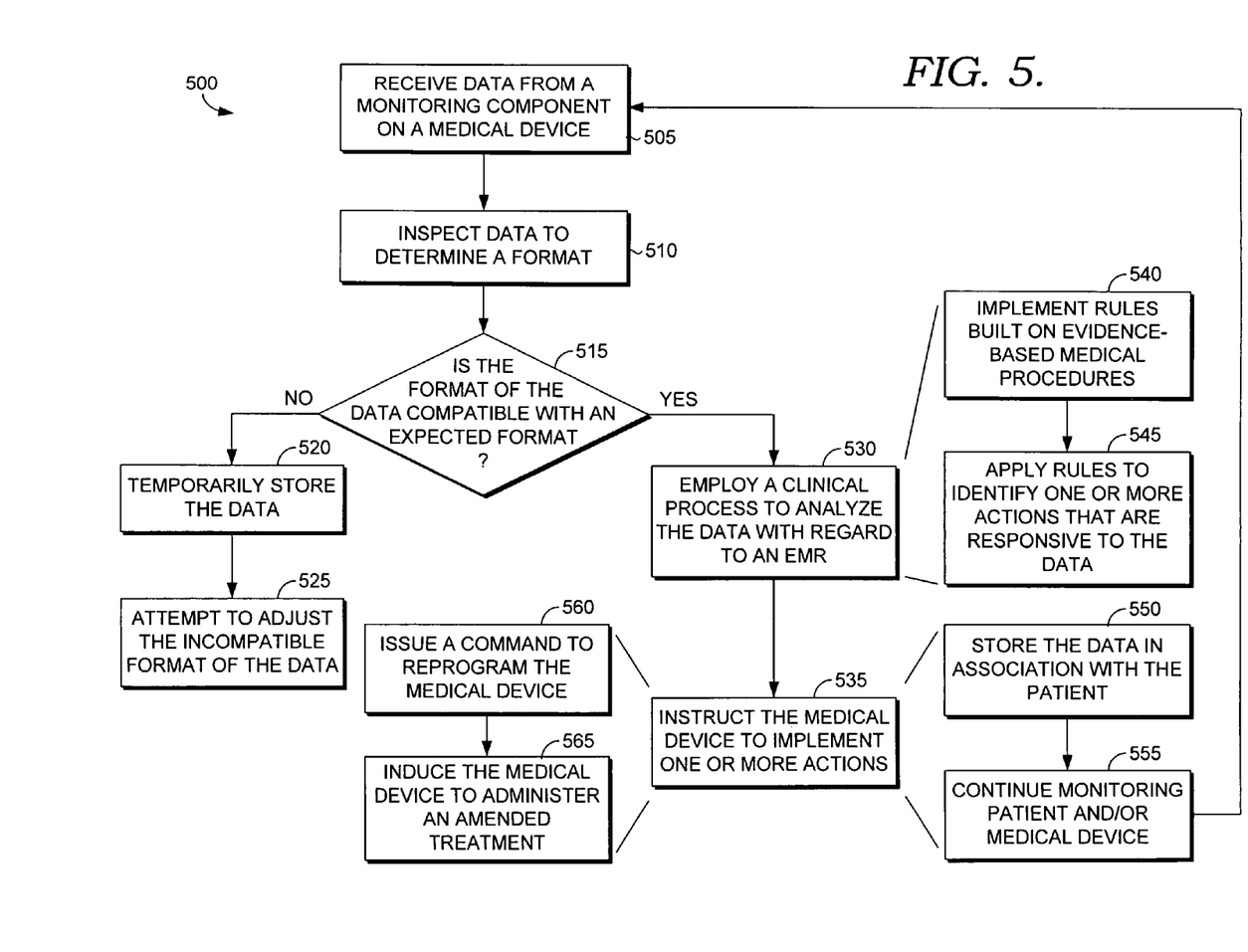
FIG. 5 is flow diagram showing an overall method for automatically managing treatment of a patient utilizing one or more medical devices operably coupled together with an evaluation device, in accordance with an embodiment of the present invention.

A particular operation of the closed-loop platform 100 of FIG. 1 will now be described with reference to FIG. 5. Generally, FIG. 5 shows a flow diagram illustrating an overall method 500 for automatically managing treatment of a patient utilizing one or more medical devices operably coupled together with an evaluation device, in accordance with an embodiment of the present invention. Although the terms "step" and "block" are used hereinbelow to connote different elements of methods employed, the terms should not be interpreted as implying any particular order among or between various steps herein disclosed unless and except when the order of individual steps is explicitly described. Initially, data is received from a monitoring component on a medical device, as depicted at block 505. In embodiments, the data may include diagnostic information that characterizes, in part, the physiological attributes obtained by monitoring the patient utilizing an in-vivo device. In other embodiments, the data may include operational-status information that describes events occurring on the in-vivo device and is typically self-reported thereby.

As depicted at block 510, the data is inspected to determine a format. As depicted at block 515, if the format of the data is incompatible with an unexpected format, the data may be stored temporarily (see block 520) or an attempt to adjust the incompatible format of the data may be launched (see block 525). As depicted at block 515, if the format of the data is compatible with an expected format, then a clinical process to analyze the data with regard to an EMR may be employed, as depicted at block 530. In embodiments, the clinical process may involve the steps of implementing rules built on evidence-based medical procedures consistent with current medical practice (see block 540), and applying the rules to identify one or more actions that are responsive to the data (see block 545). The clinical process may involve additional steps that are not illustrated in FIG. 5, but are encompassed by embodiments of the present invention, such as accessing the EMR that is associated with the patient and comparatively evaluating the data against relevant content of the EMR.

Upon analyzing the data via the clinical process, and communication may be delivered to the medical device, or any other device of the closed-loop platform, providing instructions to implement one or more actions thereby. This is depicted at block 535. These actions may include passively storing the data in association with the patient (see block 550) and continuing to monitor the patient and/or the medical device (see block 555). Further, these actions may include actively issuing a command to reprogram the medical device (see block 560), thereby inducing a medical device to administer an amended treatment to the patient (see block 565).

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope.

It will be understood that certain features and subcombinations are of utility and may be employed without reference to other features and subcombinations and are contemplated within the scope of the claims. Not all steps listed in the various figures need be carried out in the specific order described.

The invention claimed is:

1. One or more computer-readable media accommodated by an evaluation device having computer-useable instructions embodied thereon that, when executed, perform a method for observing and analyzing physiological attributes of a patient, wherein the method comprises:

receiving diagnostic information from an in-vivo device at the evaluation device wherein the diagnostic information characterizes, in part, the physiological attributes of the patient attained by monitoring the patient utilizing the in-vivo device;

accessing an electronic medical record (EMR) that is associated with the patient, wherein the EMR includes medical information that describes the patient's medical history and interactions with healthcare systems;

inspecting the EMR to discover content within the medical information that is relevant to the received diagnostic information;

accessing rules that are derived from evidence-based medical procedures;

amending a treatment being administered to the patient as a function of the relevant content and the received diagnostic information in view of the rules;

automatically causing the in-vivo device to implement the amended treatment, wherein the in-vivo device and the EMR participate in a closed-loop system that self-regulates the treatment of the patient;

upon the in-vivo device implementing the amended treatment, providing a notice from the evaluation device to the patient's insurance company that a new medication, more of a current medication, or a comparable generic medication is necessary for proper treatment of the patient;

receiving operational-status information from the in-vivo device at the evaluation device, wherein the operational-status information characterizes functional aspects of the in-vivo device;

comparing the functional aspects read from the operational-status information against device specifications accessed from a dynamically updatable source;

when the functional aspects fail to satisfy the device specifications upon comparison, causing configuration settings within the in-vivo device to be adjusted based on, in part, the device specifications;

invoking adjustment of the configuration settings of the in-vivo device by causing testing criteria within the configuration settings to be reprogrammed in accordance with the device specifications to influence either a dosage or frequency of medication being dispensed to the patient by the in-vivo device, wherein reprogramming the testing criteria affects a quality of the diagnostic information received from the in-vivo device, wherein the in-vivo device and the evaluation device participate in a closed-loop system that self-regulates the testing criteria employed by the in-vivo device;

receiving updated physiological attributes of the patient attained by monitoring the patient in accordance with the reprogrammed testing criteria.

2. The computer-readable media of claim 1, wherein the patient's medical information of the EMR comprises predefined values that are derived from expected physical attributes of the patient, and wherein comparatively evaluating the data against the patient's medical information of the EMR comprises:

comparing the diagnostic information against the predefined values;

based on the comparison, ascertaining that the diagnostic information fails to satisfy the predefined values; and providing a notification of the failure.

3. The computer-readable media of claim 2, wherein causing the in-vivo device to implement the amended treatment comprises instructing the in-vivo device to administer the amended treatment to the patient.

4. The computer-readable media of claim 1, wherein the dynamically updatable source includes an information store that maintains the predetermined device specifications, and wherein the predetermined device specifications include predefined properties of the in-vivo device.

5. The computer-readable media of claim 4, wherein causing the in-vivo device to implement the amended treatment further comprises:

examining medical-device events within the operational-status information to identify whether the in-vivo device has encountered a failure; and incident to the examination, issuing a command to reprogram the in-vivo device.

6. The computer-readable media of claim 1, wherein reprogramming testing criteria of the in-vivo device comprises causing the in-vivo device to adjust a sampling frequency of the physiological attributes of the patient.

7. The computer-readable media of claim 6, the method further comprising determining whether to accept the data from the in-vivo device, wherein the process of determining comprises:

ascertaining that a format of the data received from the in-vivo device is incompatible with an expected format;

temporarily storing the incompatibly formatted data in a memory location; and attempting to adjust the incompatible format of the data being communicated from the in-vivo device to align with the expected format.

8. The computer-readable media of claim 7, wherein the process of determining whether to accept the data from the in-vivo device further comprises performing a quality control process to validate the data is being communicated from the in-vivo device, and wherein the quality control process comprises:

reading the configuration settings of the in-vivo device from the operational-status information; and confirming that the data is accurate based on the configuration settings.

9. The computer-readable media of claim 8, wherein the process of determining whether to accept the data from the in-vivo device further comprises performing an authentication process comprising:

verifying the in-vivo device is a source of the data; and decoding a security measure imposed by the in-vivo device to protect impermissible access of the data.

10. The computer-readable media of claim 1, wherein the method further comprises primarily establishing a wireless connection between the in-vivo device and the evaluation device for receiving the data.

11. The computer-readable media of claim 10, wherein the method further comprises, upon detecting a disruption in a network carrying the wireless communication, exercising an auxiliary connection to resume communication of the data between the in-vivo device and the evaluation device.

12. The computer-readable media of claim 11, wherein the data is received by the evaluation device according to a communication scheme, wherein the communication scheme instructs the in-vivo device to transmit the data in real time, at regular intervals, or upon the issuance of a request for data.

13. The computer-readable media of claim 1, wherein reprogramming testing criteria of the in-vivo device comprises causing the in-vivo device to adjust which physiological attributes of the patient to monitor.

14. A computerized method for automatically invoking one or more actions based on an analysis of data communicated from an in-vivo device, wherein the method comprises:

receiving diagnostic information from the in-vivo device at an evaluation device wherein the diagnostic information characterizes, in part, physiological attributes of a patient attained by monitoring the patient utilizing the in-vivo device;

accessing rules that are derived from evidence-based medical procedures;

amending a treatment being administered to the patient as a function of the received diagnostic information in view of the rules;

automatically causing the in-vivo device to implement the amended treatment;

upon automatically causing the in-vivo device to implement the amended treatment, providing a notice from the evaluation device to the patient's insurance company that a new medication, more of a current medication, or a comparable generic medication is necessary for proper treatment of the patient;

receiving operational-status information communicated from the in-vivo device, wherein the operational-status information describes an operational status of the in-vivo device that is internally implanted within a patient, and wherein the operational status corresponds with device specifications of the in-vivo device maintained at a dynamically updatable source;

accessing the dynamically updateable source that maintains the device specifications;

recognizing that an update to the device specifications has occurred, wherein the updated device specifications are based on, in part, the physiological attributes of the patient attained by monitoring the patient utilizing the in-vivo device;

automatically analyzing the operational-status information by employing a clinical procedure that comprises:

(a) accessing the updated device specifications maintained at the dynamically updatable source;

(b) comparing the operational-status information of the in-vivo device against the updated device specifications; and (c) upon comparison, determining that the operational-status information of the in-vivo device does not correspond with the updated device specifications; and automatically reprogramming configuration settings stored on the in-vivo device to reflect the updated device specifications, wherein the configuration settings influence either a dosage or frequency of medication being dispensed to the patient by the in-vivo device, and wherein the in-vivo device and the dynamically updatable source participate in a closed-loop system that self-regulates the configuration settings of the in-vivo device.

* * * * *